Figure 1:
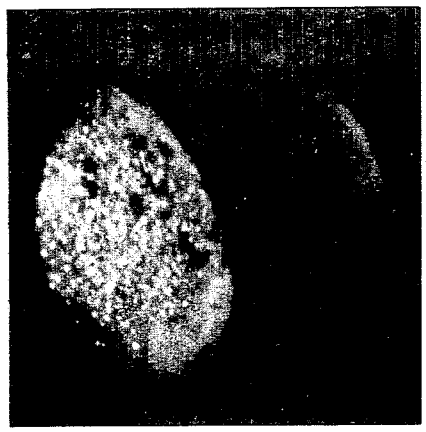

United States Patent [19]

Suzuki et al.

[11]  4,294,829
[45]  Oct. 13, 1981

[54] POWDERY PHARMACEUTICAL COMPOSITION AND POWDERY PREPARATION FOR APPLICATION TO THE NASAL MUCOSA, AND METHOD FOR ADMINISTRATION THEREOF

[75] Inventors: Yoshiki Suzuki; Hiroshi Ikura, both of Hino; Gentaro Yamashita, Koganei; Tsuneji Nagai, Tokyo, all of Japan

[73] Assignee: Teijin Limited, Osaka, Japan

[21] Appl. No.: 173,906

[22] Filed: Jul. 30, 1980

[30] Foreign Application Priority Data

Jul. 31, 1979 [JP] Japan ................................. 54-96666

[51] Int. Cl.³ ..................... A61K 31/58; A61K 31/56; A01N 43/36
[52] U.S. Cl. ................................... 424/241; 424/243; 424/330; 424/274
[58] Field of Search ................ 424/241, 243, 274, 330

[56] References Cited

U.S. PATENT DOCUMENTS 4,013,792  3/1977  Eichman et al. ..................... 424/243
4,225,597  9/1980  Finckenor .......................... 424/243

Primary Examiner—Elbert L. Roberts
Attorney, Agent, or Firm—Wenderoth, Lind & Ponack

[57] ABSTRACT

A powdery pharmaceutical composition and a powdery preparation in unit dosage form for application to the mucosa of the nasal cavity, at least about 90% of which consists of particles having an effective particle diameter of about 20 to about 250 microns, said composition comprising a lower alkyl ether of cellulose having a viscosity, determined at about 37° C. for a 2% aqueous solution thereof, of at least about 5 centipoises and a pharmaceutically effective amount of a drug; and a method for treating or preventing a human nasal disease, which comprises administering a powdery preparation in unit dosage form to the nasal cavity of a human being requiring treatment or prevention of a nasal disease through his nostrils.

19 Claims, 4 Drawing Figures

POWDERY PHARMACEUTICAL COMPOSITION AND POWDERY PREPARATION FOR APPLICATION TO THE NASAL MUCOSA, AND METHOD FOR ADMINISTRATION THEREOF

This invention relates to a powdery pharmaceutical composition for application to the mucosa of the nasal cavity. More specifically, this invention relates to a powdery pharmaceutical composition which when administered, adheres to the nasal mucosa and absorbs the mucus on the nasal mucosa to form a viscous liquid having moderate tackiness and flowability whereby the active drug contained in it is gradually and effectively absorbed through the nasal mucosa.

Heretofore, nose drops and sprays have been known as drugs intended for administration to the nasal cavity. It is difficult however to retain the active drugs of the nose drops or sprays in the nasal cavity for an extended period of time, and both of these pharmaceutical formulations are not entirely satisfactory for releasing the active drugs gradually and retain the efficacy of the drugs for a long period of time.

In an attempt to release an active drug gradually, some of the present inventors previously suggested a pharmaceutical preparation which adheres to the nasal mucosa, absorbs the mucus and gradually swells while it is adhering to the mucosa, and gradually releases the active drug from the swollen portion (U.S. Patent Application Ser. No. 17059 filed Feb. 3, 1979). This pharmaceutical preparation comprises a water-swellable and mucosa-adhesive polymeric matrix comprising about 50 to about 95% by weight of a cellulose ether and about 50 to 5% by weight of a homopolymer or copolymer of acrylic acid or a pharmaceutically acceptable salt thereof, and is characterized by having a mucosa-adhesive matrix containing both the cellulose ether and the homopolymer or copolymer of acrylic acid.

Japanese Laid-Open Patent Publication No. 84022/79 discloses a pharmaceutical composition for administration to the nose and/or lungs through nostrils, said composition comprising a mixture of beclomethasone dipropionate at least 90% by weight of which consists of particles having a size of not more than 10 microns and a powdery carrier such as an inorganic salt, organic salt or sugar. This pharmaceutical composition is not intended for slow releasing, but is characterized by the fact that the particles of the active drug are well dispersed by the aid of the powdery carrier, thus preventing difficult dispersion of the drug particles which is attributed to cohesive forces among the individual particles.

The present inventors further studied the powdery pharmaceutical composition for administration to the nasal cavity which was previously suggested by some of the present inventors. This work revealed certain facts. For example, the powdery composition adheres to the nasal mucosa to which it has been administered, stays there for an extended period of time, swells and continues to release the active drug. Thus, it is excellent in regard to slow releasing of the active drug. Since, however, the powder continues to swell while staying long on the nasal mucosa to which it has been applied, the contact of the drug in the powder with the nasal mucosa depends greatly upon the particle size of the powder. If, in an attempt to better the contact between the two, the particle size of the powder is reduced, the proportion of the powder which adheres to the nasal mucosa in spray administration to the nasal cavity decreases, and the proportion of the powder which reaches the lungs or dissipates out of the nostrils increases unnegligibly. Furthermore, the ratio of utilization of the active drug is not entirely satisfactory because the drug in the powder composition adhering to the nasal mucosa is absorbed by the diffusion of the drug through the swollen powder.

In order to provide a powdery pharmaceutical composition which is suitable for application to the mucosa of the nasal cavity, gradually releases the active ingredient over a long period of time, and shows a high availability of the active ingredient, the present inventors furthered their investigations from quite a different viewpoint from conventional nose drops and sprays as well as from the powdery pharmaceutical composition having a mucosa-adhesive matrix.

It is an object of this invention to provide a powdery pharmaceutical composition for application to the mucosa of the nasal cavity.

Another object of this invention is to provide a powdery pharmaceutical composition which when administered to the nasal cavity, releases the active ingredient over a long period of time, and shows a high availability of the active ingredient.

Still another object of this invention is to provide a powdery pharmaceutical composition which when administered to the nasal cavity, adheres to the nasal mucosa, absorbs mucus on the nasal mucosa to form a viscous liquid having moderate adhesiveness and moderate flowability, thereby covers the nasal mucosa as a substantial fluid surface, and gradually flows while slowly renewing the surface of contact with the nasal mucosa thereby to release the active ingredient over a long period of time and give a high availability of the active ingredient.

A further object of this invention is to provide a method for treating or preventing a human nasal disease, which comprises applying a powdery preparation in unit dosage form composed of the powdery pharmaceutical composition of this invention containing an agent for treating or preventing the nasal disease to a human being who requires treatment or prevention of the nasal disease.

Other objects and advantages of this invention will become apparent from the following description.

According to this invention, these objects advantages are achieved by a powdery pharmaceutical composition for application to the mucus of the nasal cavity, at least about 90% by weight of its entire particles having an effective particle diameter within the range of about 20 microns to about 250 microns, said composition comprising a lower alkyl ester of cellulose whose 2% by weight aqueous solution has a viscosity of at least about 5 centipoises at about 37° C., and a pharmaceutically effective amount of a drug.

Figure 2:
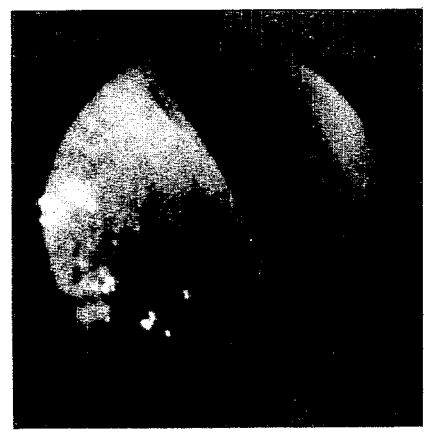
Figure 3:
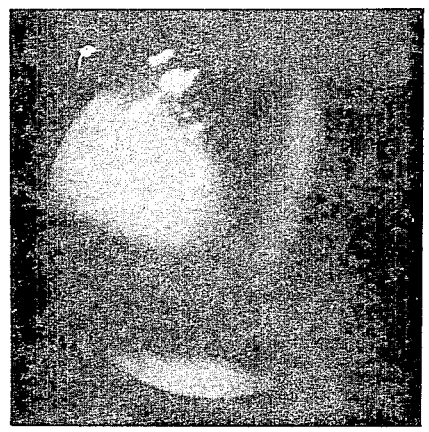
Figure 4:
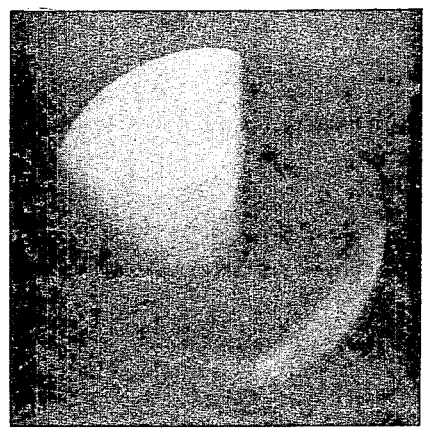

As shown in the attached FIGS. 1 to 4 (photographs taken through an endoscope), when applied to the nasal mucosa, the composition of this invention first adheres as a powder to the nasal mucosa (FIG. 1), absorbs mucus on the nasal mucosa and covers the nasal mucosa as a fluid surface (FIG. 2), slowly flows on the nasal mucosa toward a deeper portion of the nasal cavity (FIG. 3), and finally reaches a farther point which cannot be observed from the nostrils (FIG. 4). Thus, the composition of this invention is characterized in that it covers the nasal mucosa while renewing the surface of contact with the mucosa over a long period of time.

The lower alkyl ether of cellulose used in this invention results from at least partial substitution of the same or different lower alkyl ether groups for a plurality of hydroxyl groups of cellulose. The lower alkyl groups in the lower alkyl ether groups may be substituted by substituents. Preferred examples of such substituents are a hydroxyl group, and alkali metal carboxylate groups such as a sodium carboxylate group.

Examples of the optionally substituted lower alkyl groups are a methyl group, hydroxy lower alkyl groups having 2 or 3 carbon atoms, and carboxylate groups resulting from substitution of an alkali metal for the hydrogen atom of the carboxyl group of a carboxy lower alkyl group having 2 or 3 carbon atoms. Specific examples of the hydroxy lower alkyl groups are β-hydroxyethyl and β-hydroxypropyl groups, and specific examples of the carboxylate groups are carboxylate groups resulting from substitution of an alkali metal for a carboxymethyl, α-carboxyethyl or β-carboxyethyl group.

Specific examples of the lower alkyl ethers of cellulose include methyl cellulose, hydroxyethyl cellulose, hydroxypropyl cellulose, hydroxypropylmethyl cellulose, carboxymethylhydroxyethyl cellulose, and sodium carboxymethyl cellulose. Methyl cellulose, hydroxypropyl cellulose and hydroxypropylmethyl cellulose have substantially no odor and irritation and therefore are preferred for application to the nasal mucosa which is particularly sensitive to odor and irritation. Among these cellulose ethers, hydroxypropyl cellulose is especially preferred because it has the property of easily absorbing mucus from the nasal mucosa until it gives the pharmaceutical composition moderate adhesiveness and moderate flowability on the nasal mucosa.

These lower alkyl ethers of cellulose can be used either singly or in combination with each other.

Investigations of the present inventors have shown that the desirable property of the powdery pharmaceutical composition of this invention to absorb mucus from the nasal mucosa upon application thereto and to form a viscous liquid which gradually flows on the nasal mucosa can be represented by the viscosity of a 2% by weight aqueous solution of the lower alkyl ether of cellulose, which is at least about 5 centipoises, preferably about 5 to about 5000 centipoises, when measured at about 37° C., more specifically at 37° C.±0.2° C.

Thus, any of lower alkyl ethers of cellulose which have the specified viscosity can be used in this invention irrespective of its degree of ether substitution. Generally, however, those having a degree of ether substitution of 0.1 to 6, especially 0.4 to 4.6 are preferred.

The term "degree of ether substitution" denotes the total number on an average of all etheric oxygen atoms present for each of the glucose units constituting the cellulose excepting cyclic ether groups of glucose and ether groups present between adjacent glucose units.

Accordingly, hydroxypropyl cellulose having a degree of ether substitution of 3 can be composed of recurring units represented, for example, by the following formula (a) and/or (b).

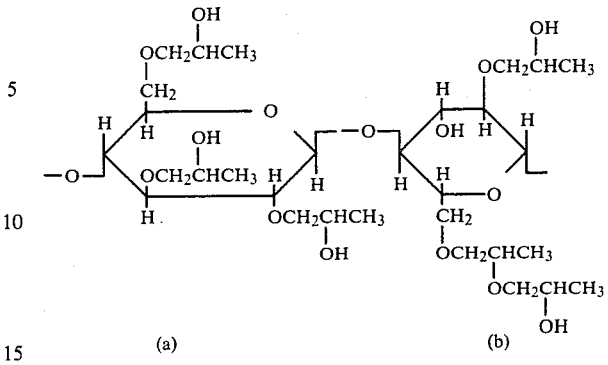

The powdery pharmaceutical composition of this invention comprises the lower alkyl ether of cellulose having the aforesaid property on the nasal mucosa and a pharmaceutically effective amount of a drug.

The drug may be selected according to a disease to which the composition is to be applied. It is important in the composition of this invention that the drug should be absorbed into the living body through the nasal mucosa and should not react with the lower alkyl ether of cellulose. Most drugs, however, have the above property although there may be some exceptions.

Preferably, drugs that can be used in the composition of this invention are solid at ambient temperature. Sometimes, liquid drugs may also be used.

Examples of such drugs include steroidal antiinflammatory agents such as hydrocortisone, predonisone, predonisolone, triamcinolone, triamcinolone acetonide, dexamethasone, betamethasone, beclomethasone, and beclomethasone dipropionate; non-steroidal anti-inflammatory agents such as acetaminophen, phenacetin, aspirin, aminopyrine, sulpyrine, phenylbutazone, mefenamic acid, sulfenamic acid, ibuprofen, ibufenac, alclofenac, diclofenac sodium, indomethacine, colchicine, and probenecid; enzymatic anti-inflammatory agents such as chymotrypsin and bromelain seratiopeptidase; antihistaminic agents such as diphenhydramine hydrochloride, chloropheniramine maleate and clemastine; anti-allergic agents (antitussive-expectorant antasthmatic agents such as sodium cromoglycate, codeine phosphate, and isoproterenol hydrochloride; antibiotics and antimicrobial agents such as tetracycline hydrochloride, leucomycin, praseomycin, penicillin, penicillin derivatives and erythromycin; chemothrapeutic agents such as sulfathiazole and nitrofurazone; local anesthetics such as benzocaine; vasoconstrictors such as phenylephrine hydrochloride, tetrahydrozoline hydrochloride, naphazoline nitrate, oxymetazoline hydrochloride and tramazoline hydrochloride; cardiotonics such as digitalis and digoxin; vasodilators such as nitroglycerin and papaverine hydrochloride; antispetics such as chlorhexidine hydrochlovide, hexylresorcinol, dequalinium chloride and ethacridine; enzymes such as lysozyme chloride, dextranase; hypoglycemics such as insulin; bone metabolism controlling agents such as calcitonin, vitamine $D_3$ and active vitamine $D_3$; hemostnts; sex hormones; hypotensives; sedatives; and anti-tumor agents.

Compositions of this invention containing steroidal anti-inflammatory agents, non-steroidal anti-inflammatory agents, antihistaminic agents, anti-allergic agents and vasoconstrictors can exhibit especially good therapeutic and prophylactic effects. Above all, compositions of this invention containing triamcinolone acetonide and beclomethasone dipropionate as the steroidal anti-inflammatory agents, indomethacine as the nonsteroidal anti-inflammatory agent, chlorpheniramine maleate and clemastine as the antihistaminic agents, ephedrine and sodium cromoglycate as the anti-allergic agents, and naphzoline nitrate as the vasoconstrictor are especially recommended by the present inventors.

Since the site of application is the nasal cavity, the composition of this invention is preferably used for the treatment and prevention of nasal diseases such as allergic rhinitis and vasomotory rhinitis. For this purpose, drugs effective for treatment or prevention of nasal diseases, such as anti-inflammatory agents, anti-histaminic agents, anti-allergic agents or vasoconstrictors, are used.

The composition of this invention comprises the lower alkyl ether of cellulose and the drug, and at least about 90% by weight of the entire particles should have an effective particle diameter between about 20 to about 250 microns.

The powdery composition of this invention having the above-specified particle size distribution, when administered to the nasal cavity through nostrils, adheres to the nasal mucosa in a high proportion, and well adheres to the inferior nasal concha, the nasal septum and the inferior meatus.

If the composition contains more than about 10% by weight of particles having an effective particle diameter of less than about 20 microns, the proportion of particles which reach the lungs or dissipate out of the nostrils at the time of spraying increases. On the other hand, if the composition contains more than about 10% by weight of particles having an effective particle diameter of more than about 250 microns, it is liable to depart from the mucosa before absorption of moisture even when it has adhered to the nasal mucosa. Accordingly, such compositions are not desirable for spraying into the nasal cavity.

Preferably, at least about 90% by weight of the particles of the composition of this invention have an effective particle diameter within the range of about 20 to about 150 microns.

In the composition of this invention having the above-specified particle size distribution, the lower alkyl ether of cellulose and the drug may form independent particles, or particles of the drug may remain adhering to the surface of particles of the cellulose ether by spraying operation. Or the drug may be dispersed as particles forming a discrete phase in the particles of the cellulose ether. Alternatively, the drug may be intimately dispersed in a well dispersed state in the particles of the cellulose ether.

The composition of this invention in which the cellulose ether and the drug form independent particles is the type generally seen when the composition contains a large amount of the drug, for example when it contains a nonsteroidal anti-inflammatory agent or anti-allergic agent whose pharmaceutically effective amount is large. This type of composition is prepared by mixing the lower alkyl ether of cellulose in which about 90% by weight of the entire particles have an effective particle diameter of about 20 to about 250 microns mechanically with the particles of the drug which have a smaller effective particle diameter.

The composition of this invention in which the particles of the drug adhere to the surfaces of the particles of the cellulose ether is the type generally seen when the composition contains a small amount of the drug and the particle size of the drug is reduced as much as possible so that the drug may be dispersed as uniformly as possible in the composition. This type of composition can be prepared by mixing the cellulose ether in which about 90% by weight of the entire particles have an effective particle diameter within the range of about 20 to about 250 microns mechanically with the drug in small particles (for example, most of which are particles having a particle diameter of 1 to 10 microns by microscopiec observation). It is not entirely clear why such a composition results. It has been found however that when the particle diameter of the drug is smaller than that of the cellulose ether, mere mixing of the two gives a composition in which the particles of the drug adhere to the surfaces of the particles of the cellulose ether, and when the composition is sprayed, a particle of the drug does not separate easily from the surface of a particle of the cellulose ether and these particles are sprayed as if it were a single particle. Accordingly, a greater portion of such a composition of this invention adheres effectively to the nasal mucosa despite the fact that it contains the drug of a small particle diameter such that if present independently, the drug will reach the lungs or dissipate out of the nostrils upon spraying.

The composition of this invention in which the drug is dispersed as particles forming a discrete phase in the particles of the cellulose ether can be prepared by mechanically mixing the particles of the cellulose ether and the particles of the drug, compressing the resulting mixture at a pressure of, say, 200 to 400 $kg/cm^2$, and pulverizing the compressed mixture so that about 90% by weight of the resulting particles have an effective particle diameter within the range of about 20 to about 250 microns. This type of composition can be provided irrespective of the content of the drug, and formed as particles each of which is composed of the cellulose ether and the drug in the integrated state. Accordingly, even under vigorous vibration, etc. during transportation, the drug and the cellulose ether do not separate from each other. A composition of this type which can be directly administered may be prepared by first preparing a composition containing the drug in an excessive amount, and diluting the composition with the cellulose ether at the time of formulation.

The composition of this invention in which the drug is dispersed intimately in a well dispersed condition in the particles of the cellulose ether can be prepared by impregnating the cellulose ether with the drug in the liquid state or with a solution of the drug in an organic solvent such as ethanol (for example, by spraying with a sprayer), and then drying the impregnated product. At this time, the particle dimater of the cellulose ether may be adjusted in advance such that about 90% by weight of the entire particles have an effective particle diameter of about 20 to about 250 microns. Alternatively, the cellulose ether may be pulverized or sieved to such a particle size distribution after impregnation, or after drying. This type of composition can also be prepared by dissolving the cellulose ether and the drug in a sufficient amount of a solvent capable of dissolving the two, such as ethanol, then evaporating off the solvent, and pulverizing the residue, and if desired, sieving the particles.

In order to improve the properties, appearance or odor of the powdery pharmaceutical composition of this invention, it may, if desired, contain at least one of the known additives such as lubricants, binders, diluents, coloring agents, odor improvers, preservatives, and surface-active agents. Examples include talc, stearic acid, stearic acid salts, and waxes as the lubricants; starch, dextrin, tragacanth gum, gelatin, polyvinylpyrrolidone and polyvinyl alcohol as the binders; starch, crystalline cellulose, dextrin, lactose, mannitol, sorbitol and anhydrous calcium phosphate as the diluents; and menthol and citrus perfumes as the odor controlling agents. These additives may be used in an amount of up to about 10% by weight. The additives may be incorporated into the composition of this invention in the same manner as in the case of preparing the composition of this invention from the cellulose ether and the drug.

According to this invention, there is provided a powdery preparation in unit dosage form from the powdery pharmaceutical composition of this invention.

When the powdery pharmaceutical composition of this invention contains a pharmaceutically effective amount of the drug suitable for use directly as a unit dosage form, it can be directly used as the powdery preparation of this invention.

If the amount of the drug contained in the powdery pharmaceutical composition of this invention is not suitable directly for a unit dosage form, the powder of this invention may be prepared by diluting the composition with the cellulose ether and/or a known diluent of the type exemplified hereinabove to prepare a powdery pharmaceutical composition of this invention containing the drug in an amount suitable for a unit dosage form, and converting it into the powdery preparation of this invention.

Because the site of application is the nasal cavity, the amount of the powdery preparation of this invention in unit dosage form is generally about 5 to about 200 mg, preferably about 10 to 100 mg. The content of the drug differs depending upon the pharmaceutically effective amount of the drug used, and upon whether it is administered at a time or in several portions at different times.

For example, it is known that while steroidal anti-inflammatory agents and anti-histaminic agents such as clemastine are generally effective in very small amounts, nonsteroidal anti-inflammatory agents and anti-allergic agents are generally effective in larger amounts. The amount known for a particular drug to be suitable for unit dosage is a measure of the content of the drug in the powdery preparation of this invention. The powder of this invention has the advantage that an equivalent effect can be obtained by using the drug in an amount smaller than the amount generally known for the drug to be suitable for unit dosage. Such an advantage is believed to be attributed to the fact that the powder of this invention absorbs mucus from the nasal mucosa, and flows gradually while covering the nasal mucosa substantially as a fluid surface.

For example, the generally known amount of beclomethasone dipropionate is about 200 to about 400 $\mu g$/body/day. It has been clinically ascertained that when beclomethasone dipropionate is incorporated into the powdery preparation of this invention, an equivalent pharmacological effect can be obtained by using it in an amount of only about 25 to about 100 $\mu g$/body/day.

Accordingly, the powdery preparation of this invention can be provided, for example, as a powder containing about 0.005 to about 1% by weight of a steroidal anti-inflammatory agent. Thus, if the amount of the powder is 40 mg, it contains about 2 to about 400 $\mu g$ of the steroidal anti-inflammatory agent.

The powdery preparation of this invention can also be provided as a powder containing about 0.1 to about 20% by weight of an anti-histaminic agent. Thus, if the amount of the powdery preparation is 40 mg, it contains about 0.04 to about 8 mg of the antihistaminic agent.

The powder may be filled in capsules, such as hard gelatin capsules, as a preferred form for administration.

The powdery preparation of this invention may be sprayed into the nasal cavity by, for example, mounting a capsule filled with the powdery preparation in a spayer equipped with a needle, piercing the capsule with the needle to provide minute holes on the top and bottom sides of the capsule, and thereafter sending air by means of a rubber ball or the like to jet out the powder.

Investigations of the present inventors have shown that by adjusting the moisture content of the powdery preparation of this invention to not more than about 9% by weight, the powdery preparation can be administered to the nasal cavity in a very good dispersed state by the aforesaid spraying method or the like without agglomeration of the particles of the powder. Accordingly, the powdery preparation of this invention preferably has a moisture content of not more than about 9% by weight.

The present invention also provides a method for treating or preventing a disease, which comprises administering the powdery preparation of this invention containing a drug effective for treatment or prevention of the disease to the nasal cavity of a human being requiring treatment or prevention of the disease, thereby causing the powder to adhere to the mucosa of the nasal cavity.

In particular, the method of this invention can be preferably applied to the treatment or prevention of nasal diseases such as allergic rhinitis or vasomotory rhinitis.

The following Examples illustrate the present invention more specifically. It should be understood that these Examples are given to explain the invention and not to limit the scope of the invention.

The "effective particle diameter" and "viscosity", used throughout the present application, are defined and measured by the following methods.

Effective particle diameter

The effective particle diameter is determined by the opening sizes of sieves. For example, a powder having an effective particle diameter (d) of $37 < d \leq 44$ passes through a sieve having an opening size of 44 microns but does not pass through a sieve having an opening size of 37 microns.

A vibratory sieve is used when the effective particle diameter of a powder is more than 37 microns, and a sonic sieve (Micro Hand Sifter SWM-2, a product of Tsutsui Rikagaku Kikai Co., Ltd.) is used when the effective particle diameter of a powder is not more than 37 microns.

The sieves used had an opening size of 500, 420, 350, 297, 250, 210, 177, 149, 125, 105, 88, 74, 63, 53, 44, 37, 25, and 20 microns, respectively.

Viscosity

A 2% by weight aqueous solution of the lower alkyl ether of cellulose is prepared by adding a predetermined amount of the cellulose ether to cold to warm water (e.g., water at about 5° to about 30° C.) and stirring the mixture, or by a method involving raising and lowering the temperature of the solution, for example by dispersing the cellulose ether in hot water at about 80° C. with stirring, and thereafter cooling the dispersion to a temperature of, say, about 5° C. to form a complete uniform aqueous solution. Either one of these method is chosen depending upon the type of the cellulose ether.

The viscosity of the 2% aqueous solution of the cellulose ether thus prepared is measured in a customary manner by using a B-type viscometer (model BL, a product of Tokyo Keiki Co., Ltd.) at 37°±0.2° C. The type and rotating speed of the rotor is chosen depending upon the viscosity of a sample solution. Generally, it is recommended to employ the type and rotating speed of the rotor according to the upper limits of the viscosity of the aqueous solution (centipoises) shown in the following table.

| Rotor No. | Rotating speed (rpm) | | | |
|---|---|---|---|---|
| | 60 | 30 | 12 | 6 |
| 1 | 100 | 200 | 500 | 1000 |
| 2 | 500 | 1000 | 2500 | 5000 |
| 3 | 2000 | 4000 | 10000 | 20000 |
| 4 | 10000 | 20000 | 50000 | 100000 |

EXAMPLE 1

In order to determine the organoleptic properties of the lower alkyl ether of cellulose upon spraying application to the nasal cavity, it was examined for odor, irritation to the nasal mucosa and adhesiveness to the nasal mucosa, and also for a feeling of discomfort due to foreign matter in the nasal cavity when the cellulose ether had absorbed mucus on the nasal mucosa.

40 mg of a powder of each of the lower alkyl ethers of cellulose shown in Table 1, at least 90% by weight of which consisted of particles having an effective particle diameter of 37 to 149 microns, was filled in a #2 hard gelatin capsule. The capsule was set in a sprayer equipped with a needle with a diameter of 0.8 mm for piercing the capsule and a rubber ball for sending air. The capsule was then pierced with the needle to provide a hole at both ends of the capsule. Then, the rubber ball was pressed to send the air, and the cellulose ether powder was jetted out from the tip of a nozzle of the sprayer. The tip of the nozzle was inserted into the nostriles of each of the volunteer patients with perennial allergic rhinitis, and the cellulose ether was sprayed into the nostrils four times for each of the left and right nostrils until all (40 mg) of the cellulose ether was consumed. The panel of the 10 patients then evaluated its odor, irritation, adhesiveness to the nasal mucosa, and a feel of foreign matter in the nasal cavity after the cellulose ether had been swollen with mucus. The results are shown in Table 1.

The various organoleptic properties were rated as follows:

Odor and irritation

A rating of ○ was given when 9 to 10 subjects of the panel reported th they had no objection to continued use of the cellulose ether as a base of a nasal spray because it was substantially free from odor and irritation. A rating of Δ was given when 6 to 8 subjects of the panel reported that although the cellulose ether had slight odor and irritation, they would accept its continued use. A rating of × was given when 5 or less subjects of the panel reported that although the cellulose either had odor or irritation, they would accept its continued use, or 3 or more subjects of the panel reported that they did not like using it continuously.

Adhesiveness to the nasal mucosa

A rating of ○ was given when within 10 minutes after spraying of the cellulose ether into the nasal cavity, the cellulose ether as a white powder scarcely dropped off from the nasal cavity in 8 or more subjects of the panel. A rating of Δ was given when a small amount of the cellulose ether powder dropped off from the nasal cavity in 8 or more subjects of the panel within the above-specified period. A rating of × was given when a considerable amount (at least about 4 mg) of the cellulose ether powder dropped off in 3 or more subjects of the panel within the above-specified period.

Feel of foreign matter in the nasal cavity

A rating of was given when 9 or 10 subjects of the panel reported that they scarcely had a feel of foreign matter. A rating of Δ was given when 6 to 8 subjects of the panel scarcely had a feel of foreign matter and 2 to 4 subjects had a feel of foreign matter. A rating of × was given when 5 or more subjects of the panel had an unpleasant feel of foreign matter.

Calcium carboxymethyl cellulose, cellulose acetate phthalate, and polyacrylic acid were used as comparisons, and the results are also shown in Table 1.

TABLE 1

| Run No. | Lower alkyl ether of cellulose | Viscosity (37° C., 2% aq. sol.; cps) | Odor | Irritation | Adhesiveness | Feel of foreign matter |
|---|---|---|---|---|---|---|
| 1 | Methyl cellulose | 650 | O | O | O | O |
| 2 | Hydroxyethyl cellulose | 1020 | Δ | O | O | Δ |
| 3 | Hydroxypropyl cellulose | 1550 | O | O | O | O |
| 4 | Hydroxypropylmethyl cellulose | 700 | O | O | O | O |
| 5 | Carboxymethylhydroxyethyl cellulose | 720 | Δ | Δ | O | Δ |
| 6 | Sodium carboxymethyl cellulose | 1850 | Δ | O | O | Δ |
| 7 (*) | Calcium carboxymethyl cellulose | — | Δ | O | Δ | X |
| 8 (*) | Cellulose acetate phthalate | — | Δ | X | X | X |
| 9 (*) | Polyacrylic acid | — | X | X | O | X |

(*) : comparisons

EXAMPLE 2

In order to determine the releasability of a drug from the cellulose ether on the nasal mucosa, a model test was performed wherein a composition composed of the cellulose ether and the drug was allowed to stand on the interface between chloroform and water, and the rate of migration of the drug to the chloroform layer was determined.

Ten milligrams of triamcinolone acetonide in which most of the particles had a size of 1 to 10 microns by microscopic observation was added to 2.0 g of hydroxypropyl cellulose at least 90% by weight of which consisted of particles having a particle diameter of 20 to 250 microns and whose 2% by weight aqueous solution had a viscosity at 37°±0.2° C. of 6, 50 and 1550 centipoises, respectively. They are well mixed in a mortar. Twenty milligrams of the resulting powder was taken, and lightly compressed by a punch and a die to form a disc having a diameter of 7 mm. A beaker having a diameter of about 4.5 cm was charged with 20 ml of chloroform, and then 20 ml of water was put into it to form a lower layer of chloroform and an upper layer of water. The disc was carried gently to the interface between them through the water layer, and allowed to stand on the water/chloroform interface with the undersurface of the disc which absorbed water being in contact with the upper surface of the chloroform layer. In this manner, five samples in the same condition were prepared using five such discs. Starting 30 minutes after standing until 2.5 hours later, 10 ml of chloroform was withdrawn by a syringe from the each beaker (sample) every 30 minutes, chloroform was evaporated off, and 5 ml of methanol containing beclomethasone dipropionate as an internal standard was added to the residue to form a solution as a sample for high-speed liquid chromatography. The amount of triamcinolone acetonide in each sample was determined by using a high-speed liquid chromatographic device (model 635, a product of Hitachi Limited) and a column having a diameter of 2.5 mm and a length of 50 cm and containing Hitachi Gel #3010 as a filler.

The proportion of triamcinolone acetonide which migrated to the chloroform layer based on the total amount of triamcinolone acetoniede (percent migration) was determined with regard to the time during which the disc was allowed stand on the water/chloroform interface. The results are shown in Table 2.

Lactose and crystalline cellulose were used as comparisons, and the results are also shown in Table 2.

It is seen that releasing of triamcinolone acetonide from the swollen hydroxypropyl cellulose showed a substantially linear relation with respect to the time, thus showing slow releasing characteristics.

Light compression of the powder into a disc was performed in order to secure much the same area of contact with the water/chloroform interface in all of the samples.

TABLE 2

| Run No. | Lower alkyl ether of cellulose | Viscosity (centipoises; at 37° C. for 2% of aq. sol.) | Standing time (hours) | | | | |
|---|---|---|---|---|---|---|---|
| | | | 0.5 | 1.0 | 1.5 | 2.0 | 2.5 |
| 1 | Hydroxypropyl cellulose | 5.5 | 23(%) | 30 | 44 | 66 | 71 |
| 2 | Hydroxypropyl cellulose | 50 | 19 | 27 | 40 | 49 | 63 |
| 3 | Hydroxypropyl cellulose | 1550 | 14 | 25 | 31 | 43 | 53 |
| 4 (*) | Lactose | — | 100 (**) | — | — | — | — |
| 5 (*) | Crystalline cellulose | — | 100 (**) | — | — | — | — |

(*) Comparisons
(**): All of the triamcinolone acetonide was released in 0.5 hour, and the composition did not show slow releasing property.

EXAMPLE 3

In order to determine the residence in the nasal cavity of the powdery preparation of this invention composed of a drug and each of various lower alkyl ethers of cellulose having each of the viscosities indicated in Table 3 and the continuity of the effect of the drug upon application of the powder to the nasal cavity, (a) the flowability of an aqueous solution of the cellulose ether on a glass plate, (b) the flowability of the cellulose ether containing saccharin on the nasal mucosa, (c) the time which elapses from administration of the powder to a patient until the effect of the drug appears, and the continuity of the effect of the drug, and (d) the flowability of hydroxypropyl cellulose on a slant agar plate were tested.

Samples used in the tests (a), (b) and (c) were prepared as follows:

2.0 g of each of the lower alkyl ethers of cellulose shown in Table 3 was taken, and dissolved in 100 ml of water. Then 20 mg of saccharin was dissolved. Furthermore, 1.25 mg of beclomethasone dipropionate was dispersed in the solution to form a dispersion of beclomethasone dipropionate. Water was evaporated from the dispersion using a rotary evaporator to obtain the lower alkyl ether of cellulose containing saccharin and beclomethasone dipropionate as a solid. The solid was dried under reduced pressure, and pulverized to form a powder at least 90% by weight of which consisted of particles having a particle diameter of 37 to 149 microns.

Specifically, the tests (a) to (d) were conducted as follows:

(a) 0.1 g of the resulting powder was dissolved in 5 ml of water to form a 2% by weight aqueous solution of the powder. 0.3 g of the aqueous solution was placed on a glass plate inclined at an angle of 10°, and the distance over which it flowed for 5 minutes was measured. The results are shown in Table 3.

(b) 40 mg of the resulting powder was filled in a hard gelatin capsule. The capsule was set in the sprayer described in Example 1, and sprayed into the left and right nostrils of five subjects. The subjects were requested to report the time which elapsed until they clearly felt the sweetness of saccharin at a deep portion of the throat. The maximum time and the minimum time reported were determined, and the results are shown in Table 3.

As a comparison, 40 mg of a lactose powder at least 90% of which consisted of particles having a particle diameter of 37 to 149 microns was mixed with 0.4 mg of saccharin particles most of which were found to have a particle diameter of about 5 to about 10 microns by microscopic observation. The mixture was filled into a hard gelatin capsule, and the capsule was administered in the same way as above. The results are also shown in Table 3.

(c) 40 mg of the powder prepared by using each of hydroxypropyl cellulose having a viscosity, determined at 37°±0.2° C. for a 2% aqueous solution thereof, of 50 and 1550 centipoises respectively, methyl cellulose having a viscosity of 650 centipoises and hydroxypropylmethyl cellulose having a viscosity of 700 centipoises was filled into a hard gelatin capsule. The capsule was set in the sprayer described in Example 1, and sprayed into the left and right nostrils of eight patients having symptoms characteristics of allergic rhinitis, such as nasal itching, sneezing and nasal blockage, and their clinical conditions were observed.

(d) 3 mg of a powder of hydroxypropyl cellulose having each of the viscosities shown in Table 4 was placed on an agar plate inclined at an angle of 15° so that it formed a circle having a diameter of about 5 mm. the distance over which the powder flowed upon swelling was measured with time. The distances measured 30 minutes after the start of the test are shown in Table 4.

As a comparison, a mixture composed of 15% of polyacrylic acid and 85% of hydroxypropyl cellulose having a viscosity, determined at 37°±0.2° C. for a 2% by weight aqueous solution thereof, of 1550 centipoises was used, and the results are also shown in Table 4.

TABLE 3

| Run No. | Lower alkyl ether of cellulose | Viscosity (centipoises at 37 ± 0.2° C. for 2% aq. sol.) | Flowing distance on the glass plate (cm) | Time elapsed until the sweetness was felt (hours) |
|---|---|---|---|---|
| 1 (*) | Hydroxypropyl cellulose | 4.5 | 15.3 | 0.2–1.2 |
| 2 | Hydroxypropyl cellulose | 5.5 | 8.4 | 2–3 |
| 3 | Hydroxypropyl cellulose | 50 | 1.5 | 5–10 |
| 4 | Hydroxypropyl cellulose | 1550 | 0.5 | 5–12 |
| 5 | Methyl cellulose | 10 | 11 | 2–4 |
| 6 | Methyl cellulose | 14 | 9.5 | 3–5 |
| 7 | Methyl cellulose | 650 | 0.5 | 5–12 |
| 8 | Methyl cellulose | 4160 | 0.3 | 6–12 |
| 9 (*) | Hydroxypropyl-methyl cellulose | 3 | 14.3 | 0.3–1.2 |
| 10 | Hydroxypropyl-methyl cellulose | 7 | 12.1 | 2–4 |
| 11 | Hydroxypropyl-methyl cellulose | 700 | 0.6 | 5–10 |
| 12 (*) | Hydroxypropyl-methyl cellulose | 14000 | did not flow | above 12 |
| 13 (*) | Lactose | — | — | 0.2–1.0 |

(*) : comparisons

TABLE 4

| Run No. | Lower alkyl ether cellulose | Viscosity (centipoises, at 37 ± 0.2° C. for 2% aq. sol.) | Flowing distance (cm) |
|---|---|---|---|
| 1 | Hydroxypropyl cellulose | 4.5 | 6.5 |
| 2 | Hydroxypropyl cellulose | 5.5 | 5.5 |
| 3 | Hydroxypropyl cellulose | 50 | 1.5 |
| 4 | Hydroxypropyl cellulose | 1550 | 0.9 |
| 5 (*) | Powder composed of 85% of hydroxypropyl cellulose and 15% of polyacrylic acid | — | Did not flow |

(*) : comparison

The results of the test (b) show that when a lower alkyl ether of cellulose having high flowability as shown by its viscosity, determined at 37°±0.2° C. for a 2% aqueous solution thereof, of less than 5 centipoises was used, the time required until the subject felt sweetness was not much different from that when lactose as a comparison was used, and the residence in the nasal cavity of the cellulose ether was not recognized, but that when a lower alkyl ether of cellulose having a viscosity, determined at about 37° C. for a 2% aqueous solution thereof, of 5 centipoises to 5000 centipoises was used, the residence time in the nasal cavity was moderately prolonged.

The results of the test (c) show that when a lower alkyl ether of cellulose having a viscosity of at least 5 centipoises was used, nasal itching was removed rapidly, and especially when a lower alkyl ether of cellulose having a viscosity of 5 centipoises to 5000 centipoises was used, attack of sternutation subsided in 3 to 6 hours in about 70% of the subjects and this effect continued for several hours. It is said that when beclomethasone dipropionate in a dose of 200 to 400 μg is administered to the nasal cavity using an aerosol containing beclomethasone dipropionate, continued administration over 2 to 3 days is required until its effect appears. In contrast, the effect of beclomethasone dipropionate applied by the method of this invention appears after one administration of as small as 25 μg of beclomethasone dipropionate. Hence, the availability of the drug is extremely high.

When the results of the tests (a) and (b) are considered in view of the results of (b) and (c), the following consclusion can be drawn.

The flowability of a lower alkyl ether of cellulose having a viscosity, determined at 37°±0.2° C. for a 2% aqueous solution thereof, of less than 5 centipoises on a glass plate or agar plate cannot suggest the moderate residence time in the nasal cavity, but the flowability of a lower alkyl ether of cellulose having a viscosity, as defined above, of 5 to 5000 centipoises on a glass plate or agar plate can suggest a moderate residence time in the nasal cavity.

EXAMPLE 4

In order to determine a suitable particle size distribution of the powder preparation of this invention, lower alkyl ethers of cellulose having different effective particle diameter distributions were prepared and sprayed into the nasal cavity, and various organoleptic tests were conducted.

Hydroxypropyl cellulose having a viscosity, determined at 37°±0.2° C. for a 2% aqueous solution thereof, of 1550 centipoises or methyl cellulose having a viscosity, as defined above, of 650 centipoises was classified by a Micro Hand Sifter SWM-2 (a product of Tsutsui Rikagaku Kakai Co., Ltd.). The classified particles were mixed to form powders having the effective particle size distributions shown in Table 6.

40 mg of each powder was filled into a #2 hard gelatin capsule. The powder in the hard gelatin capsule was sprayed into the left and right nostrils of five subjects using the sprayer described in Example 1. A feel of foreign matter in the nasal cavity owing to scattering of the powder was tested. Four subjects reported that because the powder containing 20% or 13% of particles having a particle diameter of not more than 20 microns reached the pharynx and the aditus laryngis as soon as it was sprayed into the nasal cavity, they reflexly hiccupped and felt unpleasant. Five subjects further reported that they felt unpleasant because much of the sprayed fine powder dropped out of the nostrils. As regards the powder containing more than 10% by weight of particles having a particle diameter of more than 250 microns, five subjects reported that they felt unpleasant because much of the powder dropped off from the nostrils immediately after administration as the sprayed powder readily adhered to the nasal hair upon spraying into the nasal cavity or easily separated from the nasal mucosa. Accordingly, both of these powdery preparations are undesirable for application to the nasal cavity by spraying. It has been found therefore that a powdery preparation containing at least 90% by weight of particles having an effective particle diameter of 20 to 250 microns is preferred, and a powdery preparation having at least 90% by weight of particles having an effective particle diameter of 20 to 149 microns is especially preferred.

100 mg of each of the powders shown in Table 5 was similarly filled into a #2 hard gelatin capsule, and subjected to the following test.

The capsule was set in the sprayer described in Example 1, and the nozzle of the sprayer was set at the center of a side surface of a box having a length of 100 cm, a width of 60 cm and a height of 50 cm. The rubber ball was pushed instantaneously as strongly as possible to send the air and spray the powder into the box. This operation was repeated 10 times, and then the weight of the powder which fell onto the bottom of the box from the nozzle within an area of 70 cm in length and 12 cm in width was measured and the scatterability of the powder was determined. The results are shown in Table 5 in terms of the ratio (%) of collection. The ratio of collection denotes the ratio of the amount which dropped within the above area based on the weight sprayed.

It is thus seen that a powder considered to have a preferred effective particle diameter distribution by the above organoleptic test had a ratio of collection of about 80 to about 94% by weight.

TABLE 5

| Run No. | Lower alkyl ether of cellulose | Effective particle diameter distribution (wt. %) | | | | Ratio of collection (%) |
|---|---|---|---|---|---|---|
| | | below 20 microns | 20–149 microns | 150–250 microns | above 250 microns | |
| 1 (*) | Hydroxypropyl cellulose | 20 | 80 | 0 | 0 | 62.3 |
| 2 (*) | Hydroxypropyl cellulose | 13 | 85 | 2 | 0 | 71.8 |
| 3 | Hydroxypropyl cellulose | 7 | 91 | 2 | 0 | 80.1 |
| 4 | Hydroxypropyl cellulose | 3 | 97 | 0 | 0 | 85.6 |
| 5 | Hydroxypropyl cellulose | 0 | 93 | 5 | 2 | 94.3 |
| 6 (*) | Hydroxypropyl cellulose | 0 | 80 | 5 | 15 | 95.2 |
| 7 | Methyl cellulose | 5 | 94 | 1 | 0 | 88.2 |
| 8 | Methyl cellulose | 0 | 90 | 5 | 5 | 93.6 |
| 9 (*) | Methyl cellulose | 0 | 82 | 5 | 13 | 96.3 |

(*) : Comparisons.

EXAMPLE 5

In order to determine changes with time in the condition of the powdery preparation of this invention composed of a lower alkyl ether of cellulose and a drug after spraying into the nasal cavity, the adhesion of the powder to the mucosa, its swelling and fluidization, and the state of covering the mucosa was obserbed by photographing.

Fifty grams of hydroxypropyl cellulose having a viscosity, determined at 37°±0.2° C. for a 2% by weight aqueous solution thereof, of 1550 centipoises at least 90% by weight of which consisted of particles having a particle diameter of 37 to 149 microns was put into a small-sized coating pan. While the surface of the powder was always renewed by rotating the coating pan, a solution of 0.5 g of brilliant blue in 5 ml of ethanol was sprayed little by little onto the powder. While volatilizing ethanol, this operation was repeated to form a powdery composition composed of hydroxypropyl cellulose particles containing brilliant blue dye. 10 mg of the composition was filled into a hard gelatin capsule, and the capsule was set in the sprayer described in Example 1. The powder in the capsule was sprayed into the lower portion of the ferior nasal concha of a subject, and with time, changes in the condition of the sprayed powder were observed and photographed through an endoscope. The photographs obtained are attached to the present application as FIGS. 1 to 4.

FIG. 1 shows the condition immediately after spraying in which the sprayed powder adheres to the forward end of the lower portion of the inferior nasal concha, the right half of the photograph showing the nasal septum. FIG. 2 shows the condition of the same part photographed one hour after administration, in which hydroxypropyl cellulose absorbed moisture from the nasal mucosa and turned film-like on the nasal mucosa but was not yet fluidized. FIG. 3 shows the condition of the same part photographed 2.5 hours after administration, in which the hydroxypropyl cellulose layer containing the dye became fluidized and was gradually flowing to a deeper portion while covering the mucosa of the inferior nasal concha. FIG. 4 shows the condition of the same part photographed 4 hours after administration, in which the hydroxylpropyl cellulose containing the dye was no longer present at the forward end of the lower portion of the inferior nasal concha because it had flowed down to a yet deeper part along the lower surface of the inferior nasal concha.

It is seen from this photographic observation that when the powdery composition of this invention is sprayed into the nasal cavity, it adheres to the nasal mucosa, absorbs moisture from the mucus on the nasal mucosa to form a viscous liquid having moderate adhesiveness and moderate flowability, thus covers the nasal mucosa as a substantial fluid surface, and reaches a deeper portion of the nasal cavity while slowly renewing the surface of contact with the nasal mucosa. This is probably the reason why the powdery composition of this invention continues to release the drug over an extended period of time and a high availability of the drug can be obtained.

The same test as above was performed using a capsule containing 40 mg or 60 mg of hydroxypropyl cellulose containing a dye. The powder adhered to a wider area of the nasal mucosa, and the time which elapsed until the powder went past an area viewable by an endoscope was prolonged by 2 to 3 hours. Otherwise, much the same behavior as above was observed.

EXAMPLE 6

Ten grams of hydroxypropyl cellulose having a viscosity, determined at 37°±0.2° C. for a 2% by weight aqueous solution thereof, of 1550 centipoises at least 90% by weight of which consisted of particles having a particle diameter of 37 to 149 microns was taken. One gram of it was well mixed with 10 mg of triamcinolone acetonide in a mortar while gradually adding the remainder of the hydroxypropyl cellulose to obtain a powder having triamcinolone acetonide dispersed therein uniformly 50 mg of the powder was filled into a #2 hard gelatin capsule. The capsule was set in the sprayer described in Example 1, and sprayed into the nasal cavity of 8 volunteer patients with seasonal allergic rhinitis including a severe case at a dose of 1 capsule twice a day after an observation period of 1 week. The administration was performed for 7 consecutive days, and the clinical effect was evaluated. By a physician's assessment, a beneficial effectiveness of 63% was obtained.

EXAMPLE 7

In the same way as in Example 6, capsules containing 25 μg of triamcinolone acetonide per capsule were prepared, and administered to 15 volunteer patients with perennial allergic rhinitis at a dose of one capsule once a day for 7 consecutive days. By a physician's assessment, a beneficial effectiveness of 100% was obtained.

EXAMPLE 8

Instead of the triamcinolone acetonide used in Example 6, 6.25 mg of beclomethasone dipropionate was used, and capsules each containing 40 mg of hydroxypropyl cellulose and 25 μg of beclomethasone dipropionate were prepared. The composition was administered to 10 volunteer patients with allergic rhinitis including severe and seasonal cases at a dose of 1 capsule twice a day for 7 consecutive days. By a physician's assessment, a beneficial effectiveness of 90% was obtained.

EXAMPLE 9

Instead of the triamcinolone acetonide used in Example 6, 2.5 mg of beclomethasone dipropionate was used, and capsules each containing 40 mg of hydroxypropyl cellulose and 10 μg of beclomethasone dipropionate were prepared. The composition was sprayed to 10 volunteer patients with perennial allergic rhinitis at a dose of 1 capsule twice a day for seven consecutive days. A beneficial effectiveness of 80% was obtained by physician's assessment.

EXAMPLE 10

Instead of the triamcinolone acetonide in Example 6, 50 mg of clemastine fumarate was used, and capsules each containing 40 mg of hydroxypropyl cellulose and 0.2 mg of clemastine fumarate were prepared. The composition was administered by a sprayer to 5 volunteer patients with perennial allergic rhinitis at a dose of 1 capsule once a day for seven consecutive days. By a physicians's assessment, a beneficial effectiveness of 75% was obtained.

EXAMPLE 11

One part by weight of hydropypropyl cellulose having a viscosity, determined at 37°±0.2° C. for a 2% by weight aqueous solution thereof, of 1550 centipoises, at least 90% by weight of which consisted of particles having a particle diameter of 37 to 149 microns, was mixed well with 0.01 part by weight of triamcinolone acetonide in a grinder, and the mixing was continued while gradually adding 9 parts by weight of hydroxypropyl cellulose to obtain a powder having triamcinolone acetonide uniformly dispersed therein. 50 mg of the powder was filled in a #2 hard gelatin capsule to form a powder preparation in unit dosage form.

EXAMPLE 12

100 Parts by weight of hydroxypropyl methyl cellulose having a viscosity, determined at 37°±0.2° C. for a 2% by weight aqueous solution thereof, of 16 centipoises was taken. First, one part by weight thereof was mixed well with 0.05 part by weight of triamcinolone acetonide in a mortar. The mixing was continued while adding the remainder of hydroxypropylmethyl cellulose gradually. Thus, a powder having triamcinolone acetonide uniformly dispersed therein was obtained. Then, 0.5 part by weight of magnesium stearate was added, and the mixture was molded under pressure using a small-sized tableting machine. The molded article was pulverized, and classified to form a powder at least 90% by weight of which consisted of particles having a particle diameter of about 37 to about 149 microns. 50 mg of the powder so obtained was filled into a #2 hard gelatin capsule to form a powdery preparation in unit dosage form.

EXAMPLE 13

One hundred parts by weight of methyl cellulose having a viscosity, determined at 37°±0.2° C. for a 2% by weight aqueous solution thereof, of 600 centipoises at least 90% by weight of which consisted of particles having a particle diameter of 20 to 250 microns was taken, and put into a small-sized coating pan. A solution of 0.05 parts by weight of beclomethasone dipropionate in 10 parts by weight of ethanol was sprayed little by little onto the methyl cellulose in the pan. While volatilizing the ethanol, this operation was repeated to obtain a powdery composition composed of the methyl cellulose particles and beclomethasone dipropionate. The content of beclomethasone dipropionate of the powdery composition was 320 μg/g. 31 mg of the composition was filled into a #2 hard gelatin capsule to form a powdery preparation in unit dosage form.

EXAMPLE 14

Ten parts by weight of hydroxypropyl cellulose having a viscosity, determined by 37°±0.2° C. for a 2% by weight aqueous solution thereof, of 1550 centipoises, at least 90% by weight of which consisted of particles having a particle diameter of 37 to 149 microns, was taken. First, one part by weight thereof was well mixed with 0.00625 part by weight of beclomethasone dipropionate in a mortar. The mixing was continued while gradually adding the remainder of the hydroxypropyl cellulose to obtain a powder having beclomethasone dipropionate uniformly dispersed therein. 40 mg of the powder was filled in a #2 hard gelatin capsule to form a powdery preparation in unit dosage form.

EXAMPLE 15

Ten parts by weight of the hydroxypropyl cellulose shown in Example 14 was well mixed in a mortar with 0.08 part by weight of clemastine to form a powder having clemastine unfirmly dispersed therein. 25 mg of the powder was filled into a #2 hard gelatin capsule to form a powdery preparation in unit dosage form.

EXAMPLE 16

100 Parts by weight of methyl cellulose having a viscosity, determined at 37°±0.2° C. for a 2% by weight aqueous solution thereof, of 300 centipoises was mixed with 0.5 part by weight of clemastine to form a powder having clemastine uniformly dispersed therein. Magnesium stearate (0.5 part by weight) was added to the powder, and the mixture was molded under pressure using a small-sized tableting machine. The resulting molded article was pulverized and classified to form a powder at least about 90% by weight of which consisted of particles having a particle diameter of 37 to 149 microns. 40 mg of the powder was filled into a 190 2 hard gelatin capsule to form a powdery preparation in unit dosage form.

EXAMPLE 17

Ephedrine hydrochloride (6.7 parts by weight) was added to 100 parts by weight of hydroxypropyl cellulose having a viscosity, determined at 37°±0.2° C. for a 2% by weight aqueous solution thereof, of 1550 centipoises at least 90% by weight of which consisted of particles having a particle diameter of 37 to 149 microns. They were mechanically mixed to form a powder having ephedrine hydrochloride uniformly dispersed therein. 75 mg of the powder was filled in a #2 hard gelatin capsule to form a powdery preparation in unit dosage form.

EXAMPLE 18

A powdery preparation in unit dosage form was obtained in the same way as in Example 17 except that 6.7 parts by weight of indomethacine was used as the drug.

EXAMPLE 19

A powder having chlorpheniramine maleate uniformly dispersed therein was prepared in the same way as in Example 17 except that 0.8 g of chlorpheniramine maleate was used as the drug. 50 mg of the powder was filled into a #2 hard gelatin capsule to form a powdery preparation in unit dosage form.

EXAMPLE 20

A powder having sodium cromoglycate uniformly dispersed therein was obtained in the same way as in Example 17 except that 5 parts by weight of sodium cromoglycate was used as the drug. 40 mg of the powder was filled into a #2 hard gelatin capsule to prepare a powdery preparation in unit dosage form containing 2 mg of sodium cromoglycate per capsule.

EXAMPLE 21

One hundred parts by weight of methyl cellulose having a viscosity, determined at 37°±0.2° C. for a 2% by weight aqueous solution thereof, of 650 centipoises at least 90% by weight of which consisted of particles having a particle diameter of 37 to 149 microns was mixed with 0.125 part by weight of naphazoline nitrate to form a uniform powder. 40 mg of the powder was filled into a 190 2 hard gelatin capsule to obtain a powdery preparation in unit dosage form containing 50 μg of naphazoline nitrate per capsule.

EXAMPLE 22

The effect of moisture on the jetting of a powdery preparation in a gelatin capsule in unit dosage form was tested.

100 mg of hydroxypropyl cellulose having a viscosity, determined at 37°±0.2° C. for a 2% by weight aqueous solution thereof, of 1550 centipoises, at least 90% by weight of which consisted of particles having an effective particle diameter of 37 to 149 microns, and 0.5 mg of magnesium stearate were filled into a hard gelatin capsule as unit dosage form. The capsule was allowed to stand at 25° C. for one day in an atmosphere kept at a relatively humidity of 55, 65, 70, and 75% respectively until its moisture content was equilibrated. Then, using the sprayer having a needle with a diameter of 0.8 mm used in Example 1, the capsule was subjected to a spraying test. The proportion of the powder jetted out from the capsule based on the total weight of the powder present in the capsule was determined. The results are shown in Table 6.

TABLE 6

| Run No. | Relative humidity of the atmosphere (%) | Moisture content (%) | Ratio of jetting (%) |
|---|---|---|---|
| 1 | 55 | 6.1 | 100 |
| 2 | 65 | 8.5 | 100 |
| 3 | 70 | 9.2 | 62(*) |
| 4 | 75 | 10.1 | 53(*) |

(*)When the residue in the capsule was taken out of the capsule and lightly pressed by a finger, it became a powder. When this powder was returned to the capsule, it could be sprayed.

What we claim is:

1. A powdery pharmaceutical composition for application to the mucosa of the nasal cavity, at least about 90% of which consists of particles having an effective particle diameter of about 20 to about 250 microns, said composition comprising a lower alkyl ether of cellulose selected from the group consisting of methyl cellulose, hydroxy-lower alkyl cellulose and carboxylate formed between alkali metals and carboxy-lower alkyl cellulose wherein said lower alkyls have 2 or 3 carbon atoms, said lower alkyl ether of cellulose having a viscosity, determined at about 37° C. for a 2% aqueous solution thereof, of at least about 5 centipoises and a pharmaceutically effective amount of a drug selected from the group consisting of a steroidal anti-inflammatory agent, a nonsteroidal anti-inflammatory agent, an anti-histaminic agent, an anti-allergic agent and a vasoconstrictor.

2. The composition of claim 1 wherein said lower alkyl ether of cellulose is methyl cellulose, hydroxyethyl cellulose, hydroxypropyl cellulose, hydroxypropylmethyl cellulose, carboxymethylhydroxyethyl cellulose or sodium carboxymethyl cellulose.

3. The composition of claim 1 wherein said lower alkyl ether of cellulose is methyl cellulose, hydroxypropyl cellulose or hydroxypropylmethyl cellulose.

4. The composition of claim 1 wherein said lower alkyl ether of cellulose is hydroxypropyl cellulose.

5. The composition of claim 1 wherein said lower alkyl ether of cellulose has a viscosity, determined at about 37° C. for a 2% by weight aqueous solution thereof, of about 5 to about 5000 centipoises.

6. The composition of claim 1 at least about 90% by weight of which consists of particles having an effective particle diameter of about 20 to about 150 microns.

7. The composition of claim 1 wherein said drug forms particles independent from particles of said cellulose ether, or adheres to the surface of the particles of said cellulose ether, or is dispersed as particles forming a discrete phase in the particles of said cellulose ether, or is intimately dispersed in the particles of said cellulose ether.

8. The composition of claim 1 wherein said steroidal anti-inflammatory agent is triamcinolone acetonide or beclomethasone dipropionate.

9. The composition of claim 1 wherein said nonsteroidal anti-inflammatory agent is indomethacine.

10. The composition of claim 1 wherein said antihistaminic agent is chlorpheniramine maleate or clemastine.

11. The composition of claim 1 wherein said antiallergic agent is ephedrine or sodium cromoglycate.

12. The composition of claim 1 wherein said vasoconstrictor is naphazoline nitrate.

13. A powdery preparation in unit dosage form for application to the mucosa of the nasal cavity, at least about 90% by weight of which consists of particles having an effective particle diameter of about 20 to about 250 microns, said powdery preparation comprising a lower alkyl ether of cellulose selected from the group consisting of methyl cellulose, hydroxy-lower alkyl cellulose and carboxylate formed between alkali metals and carboxy-lower alkyl cellulose wherein said lower alkyls have 2 or 3 carbon atoms, said lower alkyl ether of cellulose having a viscosity, determined at about 37° C. for a 2% by weight aqueous solution thereof, of at least about 5 centipoises and a pharmaceutically effective amount of a drug selected from the group consisting of a steroidal anti-inflammatory agent, a nonsteroidal anti-inflammatory agent, an anti-histaminic agent, an anti-allergic agent and a vasoconstrictor.

14. The powdery preparation of claim 13 wherein said drug is a steroidal anti-inflammatory agent in an amount of about 0.005 to about 1% by weight based on the weight of the powdery preparation.

15. The powdery preparation of claim 13 wherein said drug is an anti-histaminic agent in an amount of about 0.1 to about 20% by weight based on the weight of the powdery preparation.

16. The powdery preparation of any one of claims 13 to 15 which is filled in a capsule.

17. The capsule preparation of claim 16 wherein said capsule is a hard gelatin capsule.

18. A method for treating for preventing a human nasal disease, which comprises administering a powdery preparation in unit dosage form to the nasal cavity of a human being requiring treatment or preventing of a nasal disease through his nostrils, thereby adhering said powdery preparation to the nasal mucosa, said powdery preparation comprising a lower alkyl ether of cellulose selected from the group consisting of methyl cellulose, hydroxy-lower alkyl cellulose and carboxylate formed between alkali metals and carboxy-lower alkyl cellulose wherein said lower alkyls have 2 or 3 carbon atoms, said lower alkyl ether of cellulose having a viscosity, determined at about 37° C. for a 2% by weight aqueous solution thereof, of at least about 5 centipoises and a pharmaceutically effective amount of an agent for treating or preventing the nasal disease selected from the group consisting of a steroidal anti-inflammatory agent, a nonsteroidal anti-inflammatory agent, an anti-histaminic agent, an anti-allergic agent and a vasoconstrictor, at least about 90% by weight of said preparation consisting of particles having an effective particle diameter of about 20 to about 250 microns.

19. The method of claim 18 wherein the administration of said powdery preparation to the nasal cavity is performed by spraying.

* * * * *